US007370018B2

(12) United States Patent
Bryant, Jr. et al.

(10) Patent No.: US 7,370,018 B2
(45) Date of Patent: May 6, 2008

(54) SYSTEMS AND METHODS FOR PROCESSING CLAIMS IN REAL-TIME

(75) Inventors: Oliver Ross Bryant, Jr., Rex, GA (US); Scott N. Frazor, Amarillo, TX (US); James Couser Rowe, III, Sugar Hill, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 457 days.

(21) Appl. No.: 10/133,001

(22) Filed: Apr. 25, 2002

(65) Prior Publication Data

US 2002/0169955 A1 Nov. 14, 2002

Related U.S. Application Data

(60) Provisional application No. 60/286,757, filed on Apr. 25, 2001.

(51) Int. Cl.
*G06Q 99/00* (2006.01)
(52) U.S. Cl. ............................. 705/71; 705/4; 380/241
(58) Field of Classification Search .................... 705/4, 705/67, 41, 38, 1, 71; 380/241; 382/100; 713/189, 168, 185, 153; 235/383
See application file for complete search history.

(56) References Cited

U.S. PATENT DOCUMENTS

| | | | |
|---|---|---|---|
| 5,950,169 A * | 9/1999 | Borghesi et al. ................ | 705/4 |
| 6,282,522 B1 | 8/2001 | Davis et al. | |
| 6,427,020 B1 * | 7/2002 | Rhoads ....................... | 382/100 |
| 2001/0001014 A1 * | 5/2001 | Akins et al. ................ | 380/241 |
| 2001/0037224 A1 * | 11/2001 | Eldridge et al. ................ | 705/4 |
| 2002/0178370 A1 * | 11/2002 | Gurevich et al. ........... | 713/189 |

FOREIGN PATENT DOCUMENTS

GB 2329271 A * 3/1999

OTHER PUBLICATIONS

Coffey et al., The case for national health data standards, Sep./Oct. 1997, Health Affairs, v16n5, pp. 58-72.*
Claim Gear Index, Printed by Apr. 9, 2002, ,http://www.claimgear. com/Overview.htm.
Oct. 2, 2006 letter from Whitaker, Chalk, Swindle & Sawyer, LLC to Sutherland, Asbill & Brennan, LLP with enclosures of press release copies related to eRx Network, LLC.

(Continued)

*Primary Examiner*—James P. Trammell
*Assistant Examiner*—Behrang Badii
(74) *Attorney, Agent, or Firm*—Sutherland Asbill & Brennan LLP

(57) ABSTRACT

Claim processing system providing an interface to permit pharmacy and medical management systems to use the Internet to transmit third-party insurance claims on a claim-by-claim basis in real-time or near-real-time to one or more claim servers that receive insurance claim requests over the Internet in an encrypted form. The one or more claim servers decrypt the claim requests and forward them to a health network application which facilitates the submission of the claims to insurance payers and the response of the insurance payers to the requests. Payer responses are received by the claim servers, encrypted and forwarded to the pharmacy and medical management systems in real-time or near real-time.

18 Claims, 10 Drawing Sheets

OTHER PUBLICATIONS

Letter addressed to Scott Mackenzie of Per-Se Technologies from Mack Ed Swindle, Esq. of Whitaker, Chalk, Swindle & Sawyer, L.L.P. dated Jul. 21, 2006, regarding U.S. Appl. No. 10/133,001 and U.S. Appl. No. 10/439,422 (2 pages).

Letter addressed to Mac Ed Swindle, Esq. of Whitaker, Chalk, Swindle & Sawyer, L.L.P. from Griff Griffin, Esq. of Sutherland, Asbill & Brennan LLP dated Sep. 14, 2006, regarding U.S. Appl. No. 10/133,001 (2 pages).

Letter addressed to Griff Griffin, Esq. of Sutherland Asbill & Brennan LLP from Mack Ed Swindle, Esq. of Whitaker, Chalk, Swindle & Sawyer, L.L.P. dated Oct. 2, 2006 (2 pages); and attached press releases dated 2001 and 2002 (2 pages), regarding U.S. Appl. No. 10/133,001 and U.S. Appl. No. 10/439,422.

Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007 (1 page); and attached Affidavit of Ben Loy (10 pages), regarding U.S. Appl. No. 10/133,001.

Exhibit A ("Public-Key Crytography, NIST Special Publication 800-2," Apr. 1991) to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (132 pages).

Exhibit B ("Escrowed Encryption Standard (EES)," Feb. 9, 1994) to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (8 pages).

Exhibit C ("Entity Authentication Using Public Key Crytography," Feb. 18, 1997) to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (50 pages).

Exhibit D ("Internet x. 509 Public Key Infrastructure Certificate Management Protocols," Mar. 1999) to Letter addressed to Christoper J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (65 pages).

Exhibit E ("PDX 4.0 Pharmacy Manual, Canada Claims section from Jan. 2000")to Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/133,001 (4 pages).

Letter addressed to Mack Ed Swindle, Esq. of Whitaker, Chalk, Swindle & Sawyer, L.L.P. from Christopher J. Chan, Esq. of Sutherland, Asbill & Brennan LLP dated May 30, 2007, regarding U.S. Appl. No. 10/133,001 (2 pages).

Letter addressed to Mr. Kevin King of Sutherland Asbill & Brennan LLP and Mr. Paul J. Quinar of Per Se Technologies from Mack Ed Swindle, Esq. of Whitaker, Chalk Swindle & Sawyer, L.L.P. dated Feb. 12, 2007, regarding U.S. Appl. No. 11/364,987 (2 pages).

Letter addressed to Mack Ed Swindle, Esq. of Whitaker, Chalk, Swindle & Sawyer, L.L.P. from Christopher J. Chan, Esq. of Sutherland, Asbill & Brennan LLP dated Mar. 14, 2007, regarding U.S. Appl. No. 11/364,987 (2 pages).

Letter addressed to Christopher J. Chan, Esq. of Sutherland Asbill & Brennan LLP from Mack Ed Swindle, Esq. of Whitaker, Chalk, Swindle & Sawyer, L.L.P. dated May 15, 2007, regarding U.S. Appl. No. 11/364,987 (3 pages) and referenced attachments (OPUS-ISM LLC web page - 1 page) and (CareMax Connection brochure excerpt - 2 pages).

Letter addressed to Mack Ed Swindle, Esq. of Whitaker, Chalk, Swindle & Sawyer, L.L.P. from Christopher J. Chan, Esq. of Sutherland, Asbill & Brennan LLP dated Jun. 7, 2007, regarding U.S. Appl. No. 11/364,987 (2 pages).

Letter addressed to Mack Ed Swindle, Esq. of Whitaker, Chalk, Swindle & Sawyer, L.L.P. from Griff Griffin, Esq. of Sutherland Asbill & Brennan LLP dated Sep. 14, 2006 regarding U.S. Appl. No. 10/439,422 (2 pages).

Letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/439,422 (1 page).

Affidavit of Ken Hill to letter addressed to Christopher J. Chan, Esq. of Sutherland Asbill & Brennan LLP from Mack Ed Swindle, Esq. of Whitaker, Chalk, Swindle & Sawyer, L.L.P. dated May 8, 2007, regarding U.S. Appl. No. 10/439,422 (5 pages) and attached Exhibits A (5 pages) and B (49 pages).

Letter addressed to Mack Ed Swindle, Esq. of Whitaker, Chalk, Swindle & Sawyer, L.L.P. from Christopher J. Chan, Esq. of Sutherland, Asbill & Brennan LLP dated Jun. 7, 2007, regarding U.S. Appl. No. 10/439,422 (2 pages).

* cited by examiner

SYSTEMS AND METHODS FOR PROCESSING CLAIMS IN REAL-TIME

RELATED APPLICATION DATA

The present invention claims priority from U.S. Provisional Application No. 60/286,757, filed Apr. 25, 2001, titled "Systems And Methods For Conducting Electronic Transactions Over A Distributed Computer Network," the entire contents of which are incorporated herein by reference.

FIELD OF THE INVENTION

The present invention relates generally to claim processing systems, and more particularly, to claim processing systems for electronically transmitting claims to payers and for receiving responses from the payers in real-time or near real-time.

BACKGROUND OF THE INVENTION

Pharmacies, physicians, hospitals, and other healthcare service entities typically transmit claims, such as medical insurance claims, to third party payers so that the healthcare entities can be reimbursed for expenses incurred in administering goods or services associated with medical care. For instance, where a consumer purchases pharmaceuticals through a pharmacy and that consumer's pharmaceutical purchase is covered at least in part by the consumer's insurance provider, the pharmacy will typically submit a claim to the consumer's insurance provider for reimbursement. Historically, claims were written by hand and mailed to payers, which would then process the claim and pay the claim-submitting entity. Over the past fifteen years the method of substituting claims to payers has evolved, with electronic claim submissions largely taking the place of handwritten claims. Electronic claims are preferable over handwritten claims because they eliminate the need to mail or fax claims, and increase the speed with which claims are processed. Additionally, electronic claims may be entered using a practice management system commonly used by pharmacies, physicians, hospitals, or the like, which can maintain records identifying each patient or consumer along with an historical account of the treatment, drugs, procedures and other pertinent information that may be useful for providing services or drafting future claims.

Currently, many healthcare providers use a virtual private network (VPN) technology to process claims whereby they use a third party provided VPN client-side application to establish a secure connection over a variety of links, after which claims are passed in one of a variety of formats, such as in clear-text format. However, VPN technology has a number of drawbacks. First, most VPN applications only support up to 64 bit security technology. Second, multiple layers of entities handle claim communications in such a system, including a practice management system, VPN client-side application, and the transport forwarding the claim to its ultimate destination. Third, claims are usually processed in batch form in which multiple claims are transmitted simultaneously, such as at the end of the day, which delays the processing of bills for services and goods for which a claim has been submitted.

Recently some systems have been created that allow a practice management system to process claims via the Internet. For example, XGear Technologies, Inc., offers ClaimGear, which is an Internet-based practice management system that allows for insurance claim entry and electronic submission of claims to a claim clearinghouse. ClaimGear includes a thin client application residing on a client computer, where the thin client communicates over the Internet with a data center. Each time a system user wishes to save data, such as a claim, the data is transmitted over the Internet and placed into the data center database. After a claim is entered, it is submitted to payers in batch form along with all claims that were entered that day. The claims are transmitted to payers using electronic claim files. More specifically, the electronic claim files are sent to a clearinghouse that forwards the claims onto the appropriate payers. The following morning the client can view and print the clearinghouse reports of accepted and rejected claims. Although ClaimGear does allow claims to be transmitted electronically over the Internet to a clearinghouse and on to payers, the ClaimGear system does not process claims in real-time, due in part to a lack of backend connectivity to the payers. Furthermore, because claims are submitted in batch form the practice management system and claim-submitter experience a long delay in being able to process bills for the goods and services. Additionally, the data center database must be configured to collect claims for later transmission in batch form to payers, which takes up storage space at the data center and requires the data center to store claim data for extended periods of time. Furthermore, the delay in receiving a response from a payer until all claims are submitted in a batch transaction may result in a next-day retransmission of the claim, which not only delays the processing of the claim but can serve to interrupt billing and practice management.

Therefore, what is needed is a method of communicating that allows security encryption, which handles claims on a claim by claim basis, and which obviates the handling of claims by multiple entities such that payers can process and respond to claims in real-time or near real-time. What is also needed is a client system that enables conventional practice management systems to be altered such that they can communicate claims over the an always-on connection, such as the Internet, in real-time or near real-time. What is further needed is a system and method that allows claim-submitting entities, such as medical providers, to complete medical and monetary transactions more quickly, thereby facilitating better service to consumers and providing medical providers the ability to collect outstanding monies and to assess their monetary positions. What is also needed is a claim processing system and method that negates the need of a system and hardware that stores multiple claims in memory for batch transmission to a clearinghouse or payer.

SUMMARY OF THE INVENTION

Systems and methods of the present invention provide an interface to permit conventional pharmacy and medical management systems to use an always-on connection such as the Internet to transmit third-party insurance claims in real-time or near-real-time to one or more claim servers that receive insurance claim requests in an encrypted form, decrypt the requests, and forward them to a health network application which facilitates the submission of the claims to insurance payers and the response of the insurance payers to the requests. The transactions facilitated by the systems and methods of the present invention are compliant with Health Care Financing Administration (HCFA) regulations concerning the transmission of patent-specific healthcare information via the Internet. Additionally, the transactions are compliant with Health Insurance Portability and Accountability Act (HIPAA) final standards for electronic health care transactions. For instance, with respect to pharmaceutical related claims, the transactions will meet National Council for Prescription Drug Programs (NCPDP) standards, including NCPDP Telecommunication Standard Format, Version 5.1, adopted by HIPAA for electronic health care transactions and for code sets. Furthermore, using the present invention pharmacies and medical office may transmit claims for Medicaid/Medicare as well as for commercial insurance companies.

Unlike conventional systems using 800/950 number direct modem access to a health network application (thereby creating a private network communication), which requires a customer to initiate a new dial-up connection for each transaction, the systems and methods of the present invention allow a customer to have an Internet or similar always-on link to connect once with the health network application and remain connected between transactions. An always-on communication link such as the Internet provides numerous benefits to customers, including faster processing of claims transactions, more reliable connections, and the availability to access and use future-generated Internet-based products. According to one aspect of the invention, conventional practice management systems can be utilized to communicate claims over the an always-on connection.

The present invention allows payers to process and respond to claims in real-time or near real-time. Therefore, claim-submitting entities, such as medical providers, can complete medical and monetary transactions more quickly and efficiently, thereby facilitating better service to consumers and providing medical providers the ability to collect outstanding monies and to assess their monetary positions. The systems of the present invention negate the need of hardware that stores hundred of claims in memory for batch transmission to a clearinghouse or payer.

The systems of the present invention include one or more computers in communication with a Local Area Network (LAN), Wide Area Network (WAN), and/or the Internet and having one or more applications resident thereon for effecting the method of implementing the network communications as described herein. The one or more applications are referred to collectively herein as the Secure Claim Transmission Application (SCTA). The one or more claim servers through which the medical management and pharmacy systems communicate with the health network application may be located in the same computer as SCTA, or in one or more remote computers in network communication (e.g., via the Internet) with SCTA. Finally, the health network application may likewise be resident on one or more computers local to or geographically remote from one or both of SCTA and the claim servers.

Using the present invention, insurance claims may be submitted in real-time or near real-time to medical management or pharmacy systems, and transmitted over the Internet and via one or more claim servers to a health network application, which can communicate with insurance companies and/or Medicaid/Medicare to process claims in real-time or near real-time. Real-time responses are transmitted to the medical management or pharmacy systems, such that the systems receive a confirmation in real-time or near-real time that the claim has been received and processed. Additionally, the present invention enables existing systems using direct-dial access to a health network application, to communicate via the Internet while complying with HCFA security regulations, with little modification. Finally, because the present invention transmits claims on a claim-by-claim basis, an encryption key may be changed each time a claim is transmitted, which is extremely beneficial because any entity breaking the 128-bit security of the present invention would at most obtain one claim, rather than all claims, as in conventional VPN and batch claim processing systems.

According to one embodiment of the present invention, there is disclosed a claim handling system for facilitating the real-time processing of claims. The claim handling system includes a secure claim transmission application (SCTA) being configured for executing the steps of receiving a plurality of claims from a practice management system, wherein each one of the plurality of claims identifies a payer to which the claim is directed, generating a different encryption key for transmitting each one of the plurality of claims to a claim server, and receiving an encrypted claim response from the claim server for each one of the plurality of claims, wherein the encrypted claim response corresponds to a response generated by the payer to a corresponding claim transmitted to the payer by the claim server. The SCTA is further configured to execute the steps of decrypting each one of the encrypted claim responses corresponding to each one of the plurality of claims, and forwarding each of the decrypted claim responses to the practice management system, wherein each decrypted claim response is received by the SCTA in real-time or near real-time in response to the transmission to the claim server of the claim corresponding to the decrypted claim response.

According to one aspect of the present invention, the SCTA is further configured for executing the step of configuring each one of the plurality of claims for transmission to a claim server. According to another aspect of the present invention, the SCTA is further configured for executing the step of altering the format of each of one of the plurality of claims prior to their respective transmission to the claim server. According to yet another aspect of the present invention, the SCTA is further configured for executing the step of directing the transmission of each one of the plurality of claims to the claim server. Furthermore, the SCTA may be further configured for executing the step of setting up a secure session with the claim server through which at least one of the plurality of claims is transmitted to the claim server.

According to yet another aspect of the present invention, the SCTA is configured to exchange secure tokens with the claim server to set up the secure connection with the claim server. The SCTA may also be configured for executing the step of identifying a header within at least one of the plurality of claims, wherein the header identifies the at least one of the plurality of claims as directed to the payer. Additionally, the step of generating a different encryption key for transmitting each one of the plurality of claims to a claim server can further include the steps of requesting a secure connection with the claim server, receiving a secure connection response from the claim server, and examining the secure connection response to verify the authenticity of the claim server.

According to another embodiment of the invention, there is disclosed a method for facilitating the real-time processing of claims. The method includes the steps of receiving a plurality of claims from a practice management system, wherein each one of the plurality of claims identifies a payer to which the claim is directed, generating a different encryption key for transmitting each one of the plurality of claims to a claim server, and receiving an encrypted claim response from the claim server for each one of the plurality of claims, wherein the encrypted claim response corresponds to a response generated by the payer to a corresponding claim transmitted to the payer by the claim server. The method further includes the steps of decrypting each one of the encrypted claim responses corresponding to each one of the plurality of claims, and making available each of the decrypted claim responses to the practice management system, wherein each decrypted claim response is received by the practice management system in real-time or near real-time in response to the transmission to the claim server of the claim corresponding to the decrypted claim response.

According to one aspect of the invention, the method further includes the step of configuring each one of the plurality of claims for transmission to a claim server. According to another aspect of the invention, the method further includes the step of altering the format of each of one of the plurality of claims prior to their respective transmission to the claim server. According to yet another aspect of the invention, the method includes the step of directing the transmission of each one of the plurality of claims to the claim server.

The method can also comprising the step of setting up a secure session with the claim server through which at least one of the plurality of claims is transmitted to the claim server, and the step of exchanging secure tokens with the claim server to set up the secure connection with the claim server. Furthermore, according to yet another aspect of the invention, the method can include the step of identifying a header within at least one of the plurality of claims, wherein the header identifies the at least one of the plurality of claims as directed to the payer.

According to a further aspect of the invention, the step of generating a different encryption key for transmitting each one of the plurality of claims to a claim server further includes the steps of requesting a secure connection with the claim server, receiving a secure connection response from the claim server, and examining the secure connection response to verify the authenticity of the claim server. Moreover, the step of making available each of the decrypted claim responses to the practice management system can include the step of allowing the practice management system to read each of the claim responses from a serial interface to which the claim responses were written, or from a directory to which the claim responses were written.

BRIEF DESCRIPTION OF THE DRAWINGS

Figure 1:
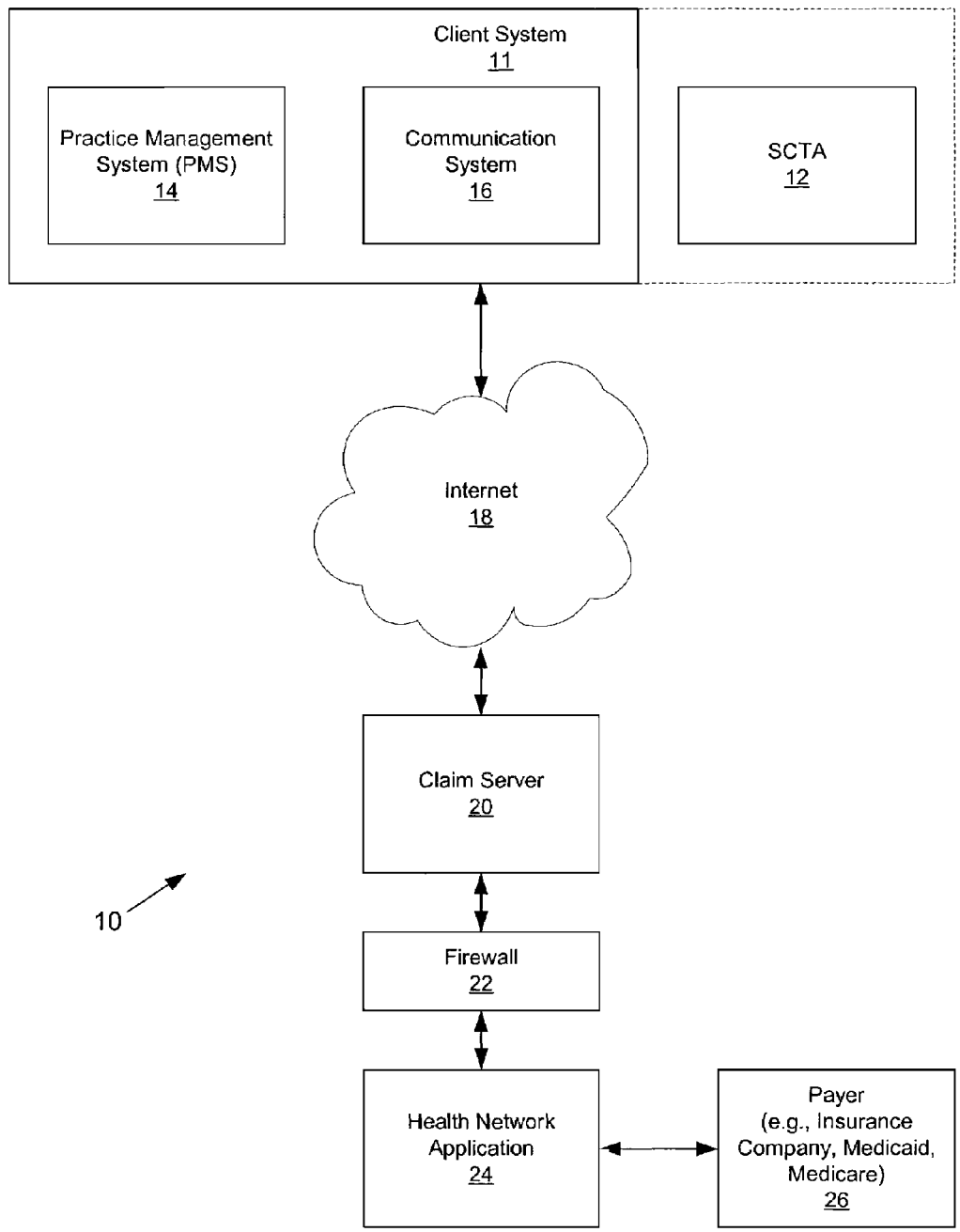

Having thus described the invention in general terms, reference will now be made to the accompanying drawings, which are not necessarily drawn to scale, and wherein:

FIG. 1 shows a system of the present invention, including a client system that transmits claims over an always-on connection such as the Internet, according to one embodiment of the invention.

Figure 2:
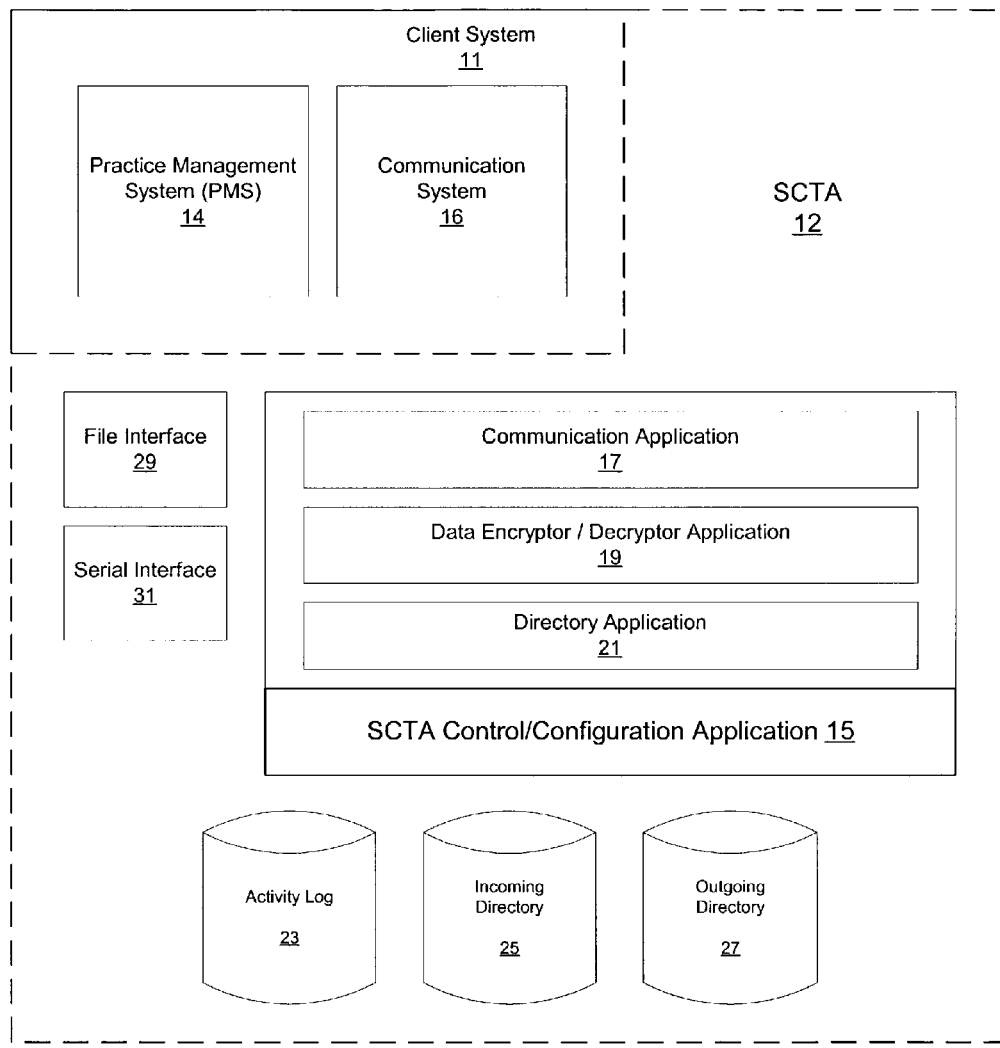

FIG. 2 shows a block diagram of SCTA, according to one illustrative embodiment of the present invention.

Figure 3A:
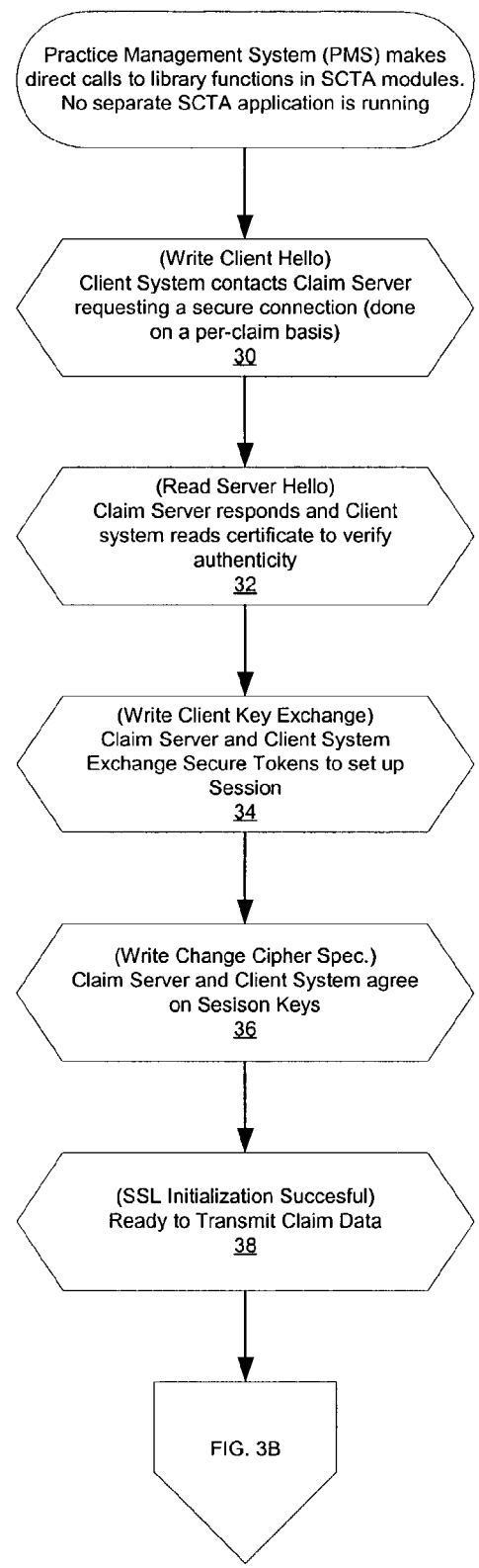
Figure 3B:
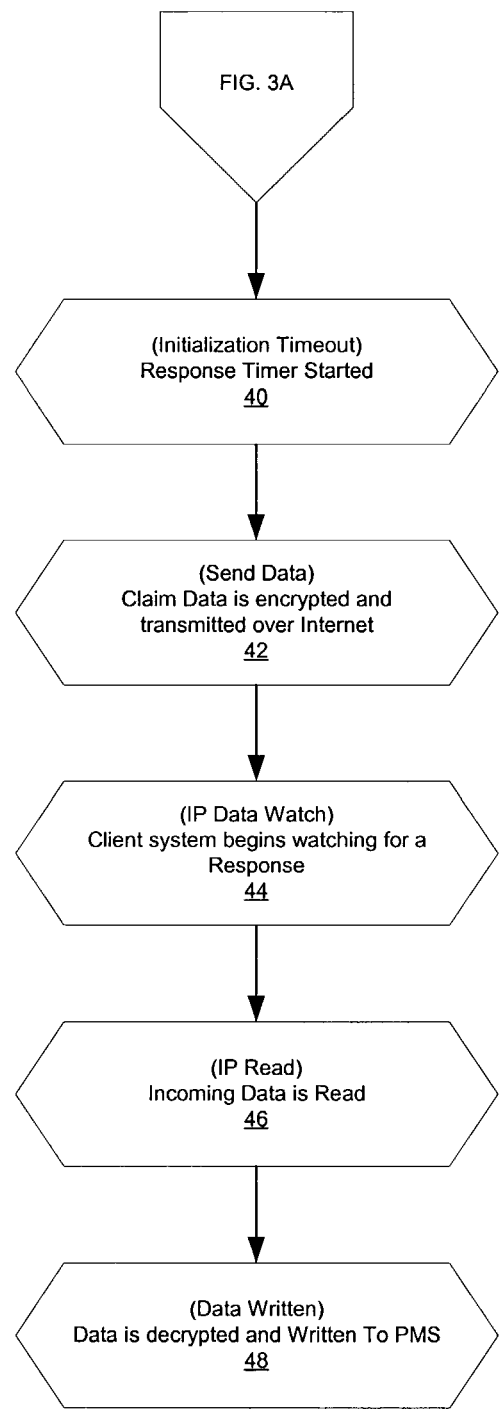

FIGS. 3A and 3B show an Application Programming Interface (API) method for facilitating claim communications between a practice management system and a health network application, according to one embodiment of the invention.

Figure 4A:
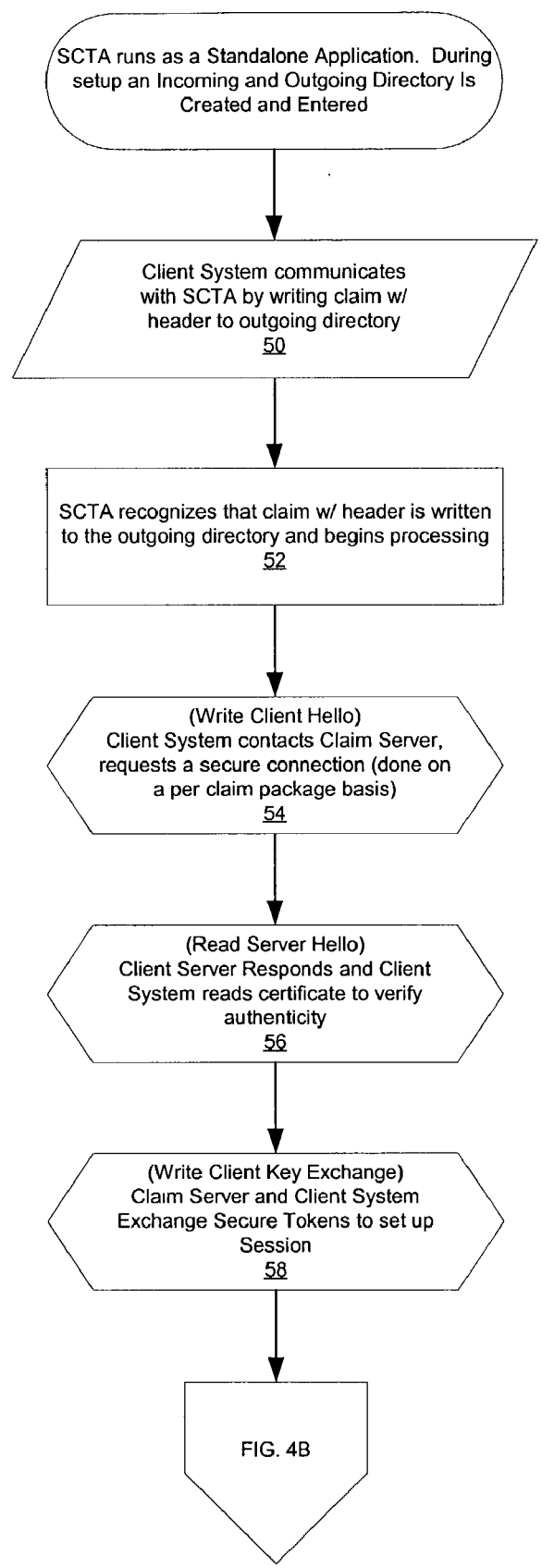
Figure 4B:
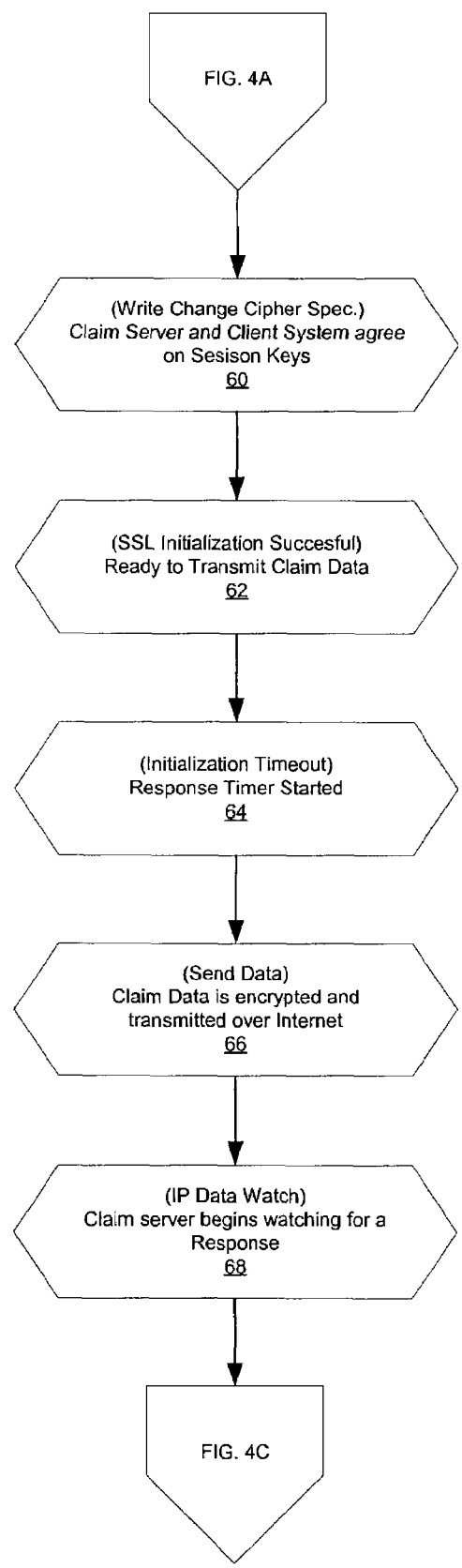
Figure 4C:
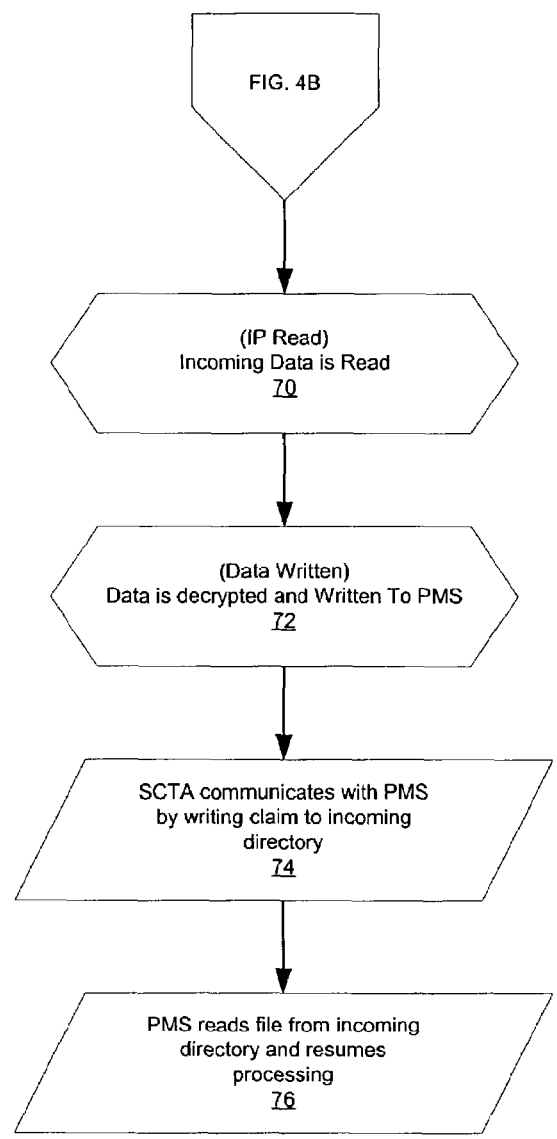

FIGS. 4A, 4B and 4C show a file-based interface method for facilitating claim communications between a practice management system and a health network application, according to one embodiment of the invention.

Figure 5A:
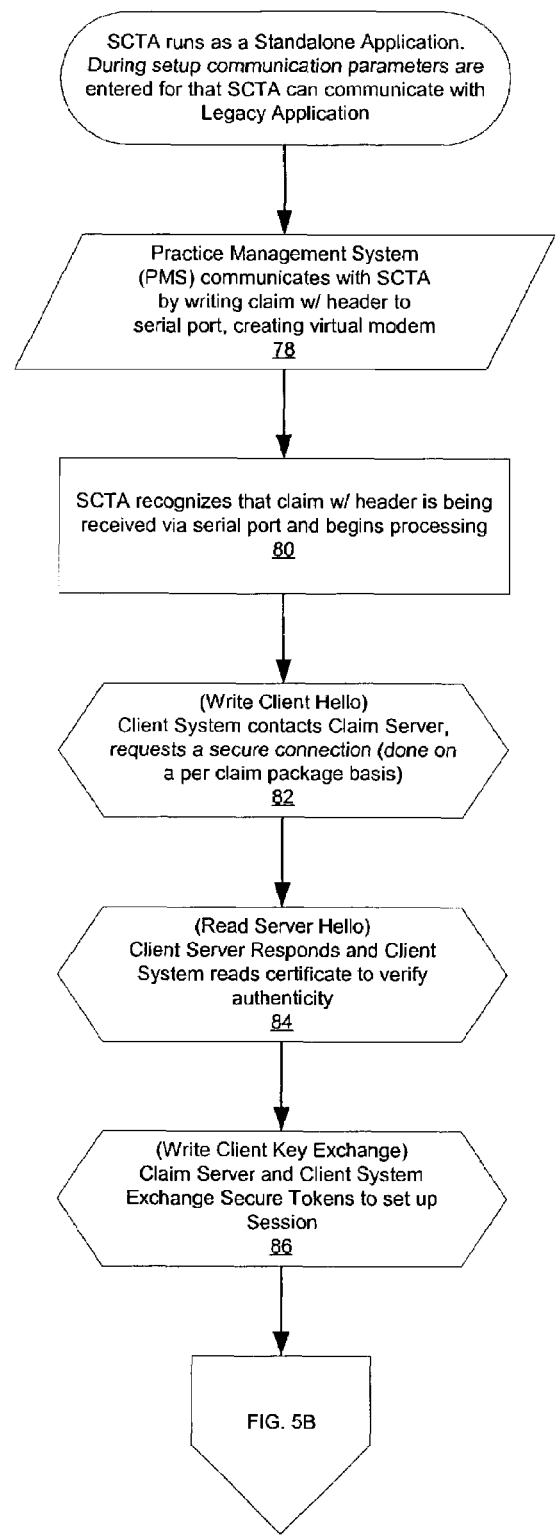
Figure 5B:
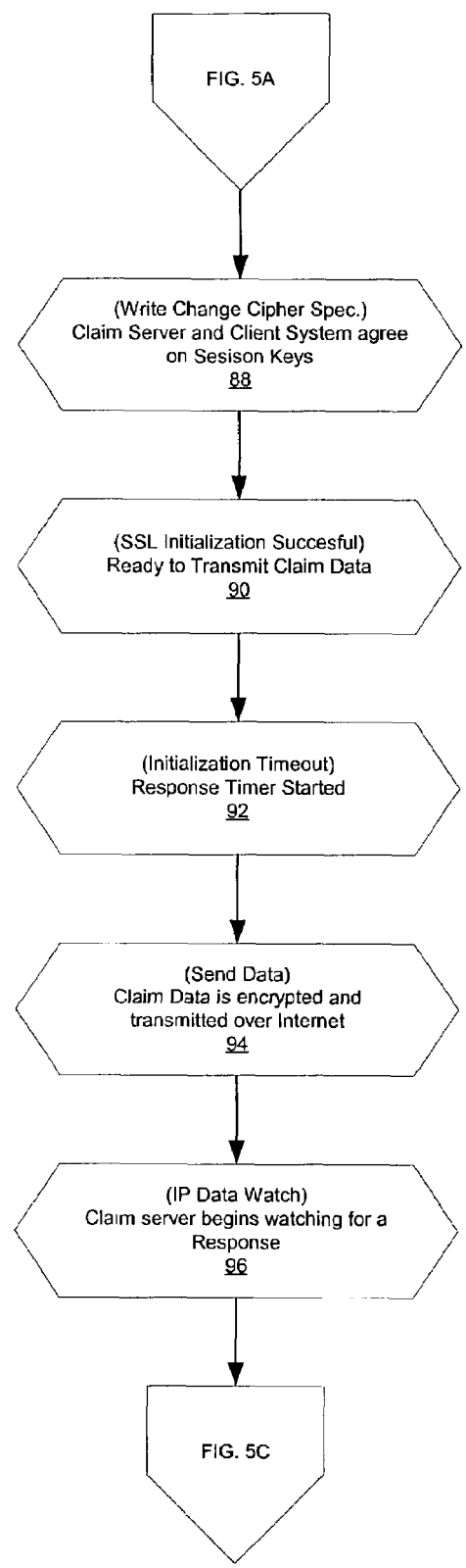
Figure 5C:
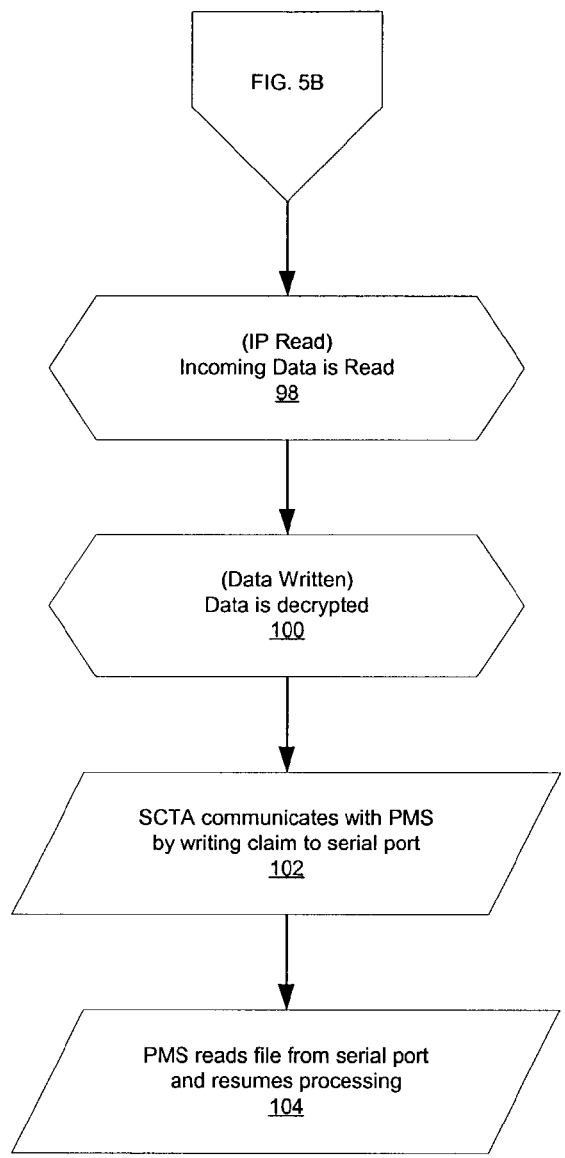

FIGS. 5A, 5B and 5C show a serial-based interface method for facilitating claim communications between a practice management system and a health network application, according to one embodiment of the invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As will be appreciated by one skilled in the art, the present invention may be embodied as a method, a data processing system, or a computer program product. Accordingly, the present invention may take the form of an entirely hardware embodiment, an entirely software embodiment or an embodiment combining software and hardware aspects. Furthermore, the present invention may take the form of a computer program product on a computer-readable storage medium having computer-readable program code means embodied in the storage medium. More particularly, the present invention may take the form of web-implemented computer software. Any suitable computer-readable storage medium may be utilized including hard disks, CD-ROMs, optical storage devices, or magnetic storage devices.

The present invention is described below with reference to block diagrams and flowchart illustrations of methods, apparatuses (i.e., systems) and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

FIG. 1 shows a claim processing system 10 according to one embodiment of the present invention. The system 10 allows healthcare or healthcare-related providers to electronically transmit claims to payers in encrypted form and to receive encrypted responses from the payers in real-time or near real-time. More specifically, the system 10 enables the real-time or near real-time electronic transmission of claims, such as pharmaceutical or medical-related insurance claims, over the Internet 18 from a client system 11 to a claim server 20 and on to a health network application 24. The health network application 24 is operative to forward the claim to a payer 26, such as an insurance company, which can respond to the claim, in accordance with HCFA regulations, in real-time or near real-time.

According to one aspect of the invention, the client system 11 comprises a pharmacy or medical management computer system that supports Transmission Control Protocol/Internet Protocol (TCP/IP) and Transport Layer Security (TLS) data encryption. TCP/IP, as is well known in the art, is used by the Internet and is the de facto standard for transmitting data over networks. TLS is similar to the Secure Socket Layer (SSL) protocol and has been widely adopted in the e-Commerce world for providing secure communications between two parties over the Internet, such as to protect exchanges between a web server and a host. Many major web browsers, including Microsoft's Internet Explorer™ and Netscape's Navigator™, support TLS and all support TCP/IP.

Referring again to FIG. 1, the client system 11 generally comprises a practice management system 14, which may be a conventional pharmacy or medical management system as is well known in the art. The client system 11 also includes a communication system 16, which enables the client system 11 to communicate claims to third parties via the Internet 18. Although the communication system 16 is illustrated as an independent component in FIG. 1, it should be appreciated by those of ordinary skill in the art that the communication system 16 may be included in whole or in part in other components within or in communication with the client system 11, such as the practice management system 14. Preferably, the communication system 16 represents a permanent or always-active high speed connection, as can be achieved using a cable modem, Digital Subscriber Line (DSL) modem, satellite modem, T1 or T3 connection, or the like. A high speed connection is advantageous to process claims in real-time and immediately upon their entry into the practice management system 14. Alternatively, however, the communication system 16 can enable the client system 11 to connect to the Internet 18 using a conventional dial-up modem.

The practice management system 14 may include a number of software components used by a practice such as a medical practice, but should include, according to the preferred embodiment, a pharmacy and medical management application (referred to hereinafter as a vendor application) for receiving claim entries and which is configured to transmit electronic claims over a VPN via dial-up access. The vendor application may be resident on one or more computers within the practice management system 14. Briefly, the vendor application includes at least one Graphical User Interface (GUI) through which claim data may be entered. Because such utilities are well known to those of ordinary skill in the art, the vendor application will not be discussed in further detail herein.

The client system 11 also includes SCTA 12, which represents a set of software utilities (and/or a computer having such software utilities residing thereon) that provide an interface to permit the practice management system 14 (e.g., pharmacy or medical management system) to transmit claims to one or more claim servers 20 via the Internet 18 using the communication system 16. According to one aspect of the invention, SCTA 12 may be an independent set of utilities or component. Therefore, SCTA 12 is preferably configured to be a separate add-on feature, software package or software utility that may be added to existing practice management systems 14 to enable existing systems to benefit from the ability to process claims electronically in real-time or near real-time. On the other hand, SCTA 12 may be a software component that can be integrated into a practice management system 14. Therefore, it should be appreciated that although SCTA 12 will be described herein as a separate add-on component to the practice management system 14, one or more SCTA functions may be executed by software residing on other elements within the client system 11. Additionally, as will be described in greater detail below, one or more SCTA 12 elements may also be distributed at locations distant from the client system 11 such that the client system 11 must access those elements using electronic communication. Regardless of the number of components used to implement SCTA 12, or the location of the SCTA software in the system 10, SCTA 12 is operative to provide the practice management system 14 access to the claim server 20, and includes functions for communications, modem setup, serial port connections, TCP/IP communication protocol, and data encryption, such as the TLS 1.0 data encryption standard.

The SCTA 12 is in communication with the practice management system 14, and more particularly, the vendor application, and is operative to carry out the encryption and decryption of claim requests and associated processing of messages generated by the practice management system 14 (or more specifically, the vendor application) so that they may be transported in compliance with HCFA regulations. According to one embodiment of the invention, SCTA 12 invokes a high level, 128-bit encrypted security connection using 128 bit TLS, or alternatively, 128 bit SSL.

Referring now to other components within the system 10 of FIG. 1, the client system 11 is in communication via the Internet 18 with a claim server 20. The claim server 20 is illustrative of one or more such servers, and is in communication with the health network application 24 through a firewall 22, as are well known in the art. According to one aspect of the present invention, the claim server 20 is a server-based application that receives insurance claim requests over the Internet 18 in encrypted form, decrypts the requests, and forwards them to the health application network 24. The health application network 24 processes the requests by communicating with payers 26, such as insurance companies or Medicaid/Medicare 26, via well-known communication methods. The health network application 24 is preferably in communication with the payer 26 such that the claims may be received and processed by the payer in real-time or near real-time. That is, it is preferred that claims submitted by the client system 11 be received and processed moments after being submitted at the client system 11 and forwarded in encrypted form to the claim server 20. Therefore, the communication links from the client system 11 to payer 26 are preferably implemented using high speed connections, such as the Internet, which allows claims to be processed on a per-claim basis to negate the need for batch processing of claims. After responses to the claim submissions generated by the payer 26 are received by the health network application 24, the responses are forwarded to the claim server 20, which encrypts the responses and forwards the responses to the claim originator (at the practice management system 14) via SCTA 12. Because SCTA 12 facilitates the processing of electronic claims while simultaneously providing real-time connectivity and security for claim submissions and responses, existing claim processing systems may transmit secure claims via the Internet 18 and receive responses in real-time or near real-time. This obviates the need for the health network application 24 to store and forward claims in batch form to the payer 26.

FIG. 2 shows a block diagram of the client system 11, including a block diagram view of components that comprise SCTA 12, according to one embodiment of the invention. As is illustrated in FIG. 2, SCTA 12 generally includes one or more applications 15, 17, 19, 21, databases 23, 25, 27, and communication interfaces 29, 31 to perform numerous the low-level functions required to provide secure, real-time Internet claim processing functionality to the practice management system 14 and to exchange claim information with the claim server 20 and health network application 24 via the Internet 18. As illustrated in FIG. 2, SCTA 12 includes a SCTA Control/Configuration Application 15 that controls the primary functions of SCTA 12, including the basic processing of serial based or file based claims through the Internet, as will be described in detail below with respect to FIGS. 4 and 5. The SCTA Control/Configuration Application 15 also controls the manner in which SCTA 12 communicates with the other components within the client system 11 as well as the manner in which elements within SCTA 12 communicate. Additionally, the SCTA Control/Configuration Application 15 serves as a core utility to control configuration settings, such as details of the file and serial interfaces 29, 31 and TCP/IP connection settings. Finally, the Control/Configuration Application 15 can also log errors and activity in an activity log 23 or historical database for later consideration, for instance, by a system administrator.

As shown in FIG. 2, SCTA 12 also includes a communication application 17, data encryptor/decryptor application 19 and directory application 21. The communication application 17 generally controls messages transmitted to and from SCTA 12 and includes functions for communications, modem setup, and serial port connections. The communication application 17 communicates with the file and serial interfaces 29, 31 to implement file and serial based communication exchange, as are described in greater detail below. The communication application 17 also controls the transmission of assembled packets, a plurality of which comprise electronic claims, to the claim server 20 and the receipt of inbound packets, a plurality of which comprise an encrypted claim response, from the claim server 20. The communication application 17 can also control messaging between elements within SCTA 12. For instance, according to another illustrative example, when a claim is generated by the practice management system 14 and forwarded to SCTA 12, the communication application 17 will operate to forward the claim to the data encryptor/decryptor application 19 so that it may be encrypted prior to its transmission via the Internet. Although the SCTA Control/Configuration Application 15 may receive the unencrypted claim, it may instruct the communication application 17 where the claim should be forwarded. It should be appreciated that the communication application 17, like the other elements within SCTA 12, may be combined with any other elements within SCTA 12. Therefore, the functions of the communication application 17 may also or alternatively reside in the other SCTA elements, such as the SCTA Control/Configuration application 15.

Next, the data encryptor/data decryptor application 19 encrypts and decrypts claims transmitted via the Internet. Preferably, the application 19 implements a 128 bit SSL or TLS data encryption standard to ensure that the claim data will be controlled within the system 10. It should be appreciated that the data encryptor/decryptor application 19 should encrypt and decrypt information in compliance with federal standards. As such, it is advantageous for the data encryptor/decryptor application 19 to be a separate module or application within SCTA 12 so as to allow updates as are necessary to comply with transmission guidelines, rules and laws.

Also illustrated within SCTA 12 in FIG. 2 is a directory application 21, which is utilized to manage the incoming and outgoing directories 25, 27. SCTA 12 supports three general methods of exchanging messages with the practice management system 14 of the client system 11. These three general include a file based method, serial based method and API method, and are each described below in the block diagram flow charts of FIGS. 3-5. As will be explained in greater detail below, the directory application 21 controls the incoming and outgoing directories 25, 27 which are used to implement the file-based method described with respect to FIG. 4.

Generally, the numerous functions of SCTA 12 include: initiating a secure TCP/IP session connection across the Internet with a claim server 20 using a Secure Socket Layer (SSL) connection (implemented by the communication application 17); capturing formatted (e.g., NCPDP-formatted) claim transaction messages that are created by the practice management system 14 (implemented by the communication application 17, interfaces 29, 31 and/or the SCTA Control/Configuration Application 15); encrypting captured outbound claim messages using data encryption (e.g., Transport Layer Security (TLS) 1.0 data encryption standard) (implemented by the data encryptor/decryptor application 19); assembling or embedding encrypted claim data into IP packets ready for Internet transport (implemented by the SCTA Control/Configuration Application 15 and the data encryptor/decryptor application 19); transmitting assembled packets to the claims server 20 (implemented by the communication application 17); receiving inbound packets transmitted from the claims server 20 (implemented by the communication application 17); disassembling received IP packets to extract embedded and encrypted formatted (e.g., NCPDP-formatted) response messages (implemented by the communication application 17 and the SCTA Control/Configuration Application 15); decrypting formatted response messages (implemented by the data encryptor/decryptor application 19); and conveying the formatted response message to the medical management or pharmacy system 14 (implemented by the communication application 17, interfaces 29, 31 and/or the SCTA Control/Configuration Application 15).

Therefore, it should be appreciated that SCTA 12 performs all of the tasks required to exchange claims information with the health network application 24 via the Internet 18. Thus, adding SCTA 12 to conventional direct dial up medical management and pharmacy systems (using 800/950 number direct access) to effect Internet access to the Health Network Application is simple due to the fact that very little modification is necessary to the medical management and pharmacy systems because SCTA 12 effects the necessary functions to allow the systems to use the Internet 18.

FIGS. 3-5 illustrate the three methods used by SCTA 12 for receiving, encrypting and forwarding claim messages, including steps executed in exchanging messages with the practice management system 14 to facilitate encryption. According to one aspect of the invention, the practice management system 14 must send and receive claim transaction messages that are formatted to standards suitable to the health network application 24, which ultimately receives and processes the claim transaction messages. According to one aspect of the present invention, the claim transaction messages that are sent and received are formatted according to NCPDP Version 3.2 standards, as are well known in the art.

It will be appreciated by those of skill in the art that where a practice management system exists that can create and interpret the formatted transactions, to enable such a system to use Internet access the only additional requirement is for the system to be able to transmit the formatted messages to and from SCTA 12 resources. The SCTA 12 resources can then perform the remaining functions to securely communicate each independent claim message individually with the health network application 24 via the Internet 18 and the claim server 20. Therefore, the present invention enables existing systems using direct-dial access to a health network application, to communicate via the Internet while complying with HCFA security regulations, with little modification. However, the invention is not limited to facilitating Internet communication of convention VPN systems, as the present invention can be employed in new systems not previously configured for direct-dial communications with the health network application 24. It should also be appreciated that the present invention allows both types of communications to take place (i.e., VPN and Internet), which may be desirable where Internet access cannot be obtained. Finally, it should be appreciated that although the below examples refer to NCPDP as the preferred format for messages, any format can be used so long as it can be received and interpreted by the health network application 24, either with or without the aid of additional software and/or hardware not illustrated herein.

FIGS. 3A and 3B show an API method performed by SCTA 12 for processing communications between with the practice management system 14 and health network application 24. Generally, an API, as is well known in the art, allows the functionality of a pre-built software module to be accessed through well-defined data structures and subroutine calls. Although APIs may be defined for private internal code, network APIs typically are the public entry points to libraries that hide low-level details of computer networking.

In the API mode, the practice management system 14 makes direct calls to library functions (DLL functions) of the SCTA 12 to control the operation of SCTA 12, and no separate SCTA 12 application is running. In this embodiment the practice management system 14 controls claim message packaging, while the lower level mechanics of the Internet connection and encryption are still handled by SCTA 12 and therefore remain transparent to the practice management system 14. This offers enhanced flexibility the performance of the client system 11 but requires custom coding at the practice management system 14. Thus, SCTA 12 is passive in this embodiment, and is not clearly presented in the block process flow shown in FIGS. 3A and 3B.

According to the API method, the client system 11 contacts a claim server 20, requesting a secure connection such that a claim transaction message (also referred to herein simply as a claim) can be transmitted to the claim server (block 30). After the claim server 20 responds and the claim server's authenticity is verified (block 32), the claim server 20 and client system 11 exchange secure tokens to set up a session (block 34). Next, to encode the communication the claim server 20 and client system 11 agree on session keys (block 36). After a Secure Socket Layer is initialized (block 38), a response timer is initialized and started (block 40), as is shown in FIG. 3B, and data is encrypted and forwarded over the Internet (block 42), and the client system 11 waits for a response (block 44). The present invention offers a distinct advantage over prior art systems due to the fact that each claim is encrypted individually using a unique encryption key, as any entity breaking an encryption code would at most intercept data contained within one claim.

Next, the claim server 20 decrypts the claim transaction message and forwards the decrypted claim transaction message through the firewall 22 to the health network application 24, which forward the claim transaction message to the payer 26. The payer 26 responds to the claim transaction message and transmits the response back through the health network application 24 and firewall to the claim server 20. The claim server 20 receives the response and encrypts it in preparation for its transmission to the client system 11. One advantage of the present invention is that each of these transactions occurs in real-time on a claim by claim basis such that should a message be intercepted or dropped only one claim may be lost or exposed.

Referring again to the flowchart of FIG. 3B, after a response if received, SSL is called to read and process the response (block 46), including decrypting the response data and writing the data to storage devices (e.g., ROM or RAM devices) in the practice management system (block 48).

The API method allows enhanced performance and allows the practice management system 14 to control message packaging. However, this method requires custom coding such that SCTA can be called upon to provide the TCP/IP settings and optionally, session ID information. Nevertheless, in this mode the low-level mechanics of the Internet connection are transparent to the practice management system 14. Typically, the API method is used to directly exchange message data via memory buffers (within the activity log or within another SCTA 12 memory buffer not illustrated in FIG. 2) of SCTA 12 and the practice management system 14. However, the API also supports the exchange of message data via a disk file or serial port.

Next, FIGS. 4A, 4B and 4C show a file-based interface method for processing communications between with the practice management system 14 and health network application 24. In this example, SCTA 12 runs as a standalone application, and during a setup process a pre-determined incoming and outgoing directory structure is created and entered. In this mode, the SCTA 12 writes each outbound claim transaction message to a specified inbox file maintained within the incoming directory 25 and receives and reads the inbound claim response message from a specified SCTA 12 outfox file maintained within the outgoing directory 27, as is controlled by the directory application 21. Therefore, unlike the embodiment discussed with respect to FIGS. 3A and 3B, one or more SCTA 12 applications are actively involved in forwarding and receiving messages to the claim server 20.

According to this aspect of the invention, SCTA 12 resources can be configured to automatically monitor the inbox file for activity and process each new message as it appears. Preferably, SCTA 12 deletes the inbox file after each message is processed. SCTA 12 resources also write the corresponding response message to the specified outfox file where it can be read by the practice management system 14 or vendor's application (which can delete the file after reading the message). Using this method, the Internet connection is transparent to the practice management system 14.

As illustrated in FIG. 4A, the client system 11 communicates with SCTA 12 by creating a claim with a header and transmitting it to the outgoing directory stored within the outgoing directory 27 (block 50). T he header is an identifying header that is required in addition to any header embedded within the claim transaction message. The header allows SCTA 12 to identify, encrypt and decrypt the message, and return any response (which will also include the header) to the client system 11. Next, the file interface 29 and/or SCTA Control/Configuration Application 15 recognize that the claim and header have been written to the outgoing directory 27 and begins to process the claim transaction message according to session and TCP/IP settings stored within SCTA 12 (block 52). Thereafter, the client system 11 contacts the claim server 20, requesting a secure connection such that a claim transaction message can be transmitted to the claim server (block 54). After the claim server 20 responds and the claim server's authenticity is verified (block 56), the claim server 20 and client system 11 exchange secure tokens to set up a session (block 58).

Referring now to FIG. 4B, to encode the communication the claim server 20 and client system 11 agree on session keys (block 60). After a Secure Socket Layer is initialized (block 62), a response timer is initialized and started (block 64). The response timer may be a separate component located within the SCTA 12 and used to interrupt the system and process where a pre-established length of time has passed before a response is received. Thereafter, the claim transaction message (also referred to herein as the claim) is encrypted and forwarded over the Internet (block 66) to the claim server 20. The claim server 20 decrypts the claim transaction message and forwards the decrypted claim transaction message through the firewall 22 to the health network application 24, which forward the claim transaction message to the payer 26. The claim server 20 waits for a response (block 68) from the payer 26, which responds to the claim transaction message and transmits the response back through the health network application 24 and firewall to the claim server 20. The incoming response data is read by the claim server 20, encrypted, forwarded to SCTA 12, decrypted and written to the practice management system 14 (blocks 70, 72). Next, the SCTA 12 writes the claim response to the incoming directory, from which the practice management system 14 can read the claim response (blocks 74, 76).

FIGS. 5A, 5B and 5C show a serial-based interface method for processing communications between with the practice management system 14 and health network application 24. This implementation utilizes a modem cable connection (as communication link 28) between the practice management system 14 and SCTA 12, which may be on a separate system or computer. In this embodiment, the management application sends outbound claim transaction messages to and receives inbound claim responses from a serial port used to connect with SCTA 12. SCTA 12 resources capture the message from a specified serial port on the SCTA system and write the response message back to the serial port, causing the response to appear at the practice management system's 14 serial port. In this embodiment SCTA operates the communication system 16 (which may be in remote communication with and remotely located from the practice management system 14, or alternatively incorporated within SCTA 12) to communicate with the claim server, such that the Internet connection is transparent to the practice management system 14.

As illustrated in FIG. 5A, the client system 11 communicates with SCTA 12 by creating a claim with a header and transmitting it to the serial interface 31 of the SCTA 12, which can comprise a serial port (block 78). The header is an identifying header that is required in addition to any header embedded within the claim transaction message. The header allows SCTA 12 to identify, encrypt and decrypt the message, and return any response (which will also include the header) to the client system 11. Next, the file interface 29 and/or SCTA Control/Configuration Application 15 recognize that the claim and header is being received via the serial interface 31 and begins to process the claim transaction message according to session and TCP/IP settings stored within SCTA 12 (block 80). Thereafter, the client system 11 contacts the claim server 20, requesting a secure connection such that a claim transaction message can be transmitted to the claim server (block 82). After the claim server 20 responds and the claim server's authenticity is verified (block 84), the claim server 20 and client system l1 exchange secure tokens to set up a session (block 86).

Referring now to FIG. 5B, to encode the communication the claim server 20 and client system 11 agree on session keys (block 88). After a Secure Socket Layer is initialized (block 90), a response timer is initialized and started (block 92), as was discussed above with respect to FIG. 4A. Next, the claim transaction message (also referred to herein as the claim) is encrypted and forwarded over the Internet (block 94) to the claim server 20. The claim server 20 decrypts the claim transaction message and forwards the decrypted claim transaction message through the firewall 22 to the health network application 24, which forward the claim transaction message to the payer 26. The claim server 20 waits for a response (block 96) from the payer 26, which responds to the claim transaction message and transmits the response back through the health network application 24 and firewall to the claim server 20.

Referring now to FIG. 5C, the incoming response data is read by the claim server 20, encrypted, forwarded to SCTA 12 and decrypted (blocks 98, 100). The decrypted data is then written to serial interface 31 (block 102), from which the practice management system 14 can read the claim response (block 104).

Using the present invention, insurance claims may be submitted to medical management or pharmacy systems, and transmitted over the Internet and via one or more claim servers to a health network application, which can communicate with insurance companies and/or Medicaid/Medicare to process claims. Additionally, the present invention enables existing systems using direct-dial access to a health network application, to communicate via the Internet while complying with HCFA security regulations, with little modification. Finally, because the present invention transmits claims on a claim-by-claim basis, an encryption key may be changed each time a claim is transmitted, which is beneficial because anyone breaking the 128-bit security of the present invention would at most obtain one claim, rather than all claims, as in conventional VPN systems.

The present invention also allows payers to process and respond to claims in real-time or near real-time on a claim-by-claim basis. Therefore, claim-submitting entities, such as medical providers, can complete medical and monetary transactions more quickly and efficiently, thereby facilitating better service to consumers and providing medical providers the ability to collect outstanding monies and to assess their monetary positions. The present invention negates the need of hardware that stores hundred of claims in memory for batch transmission to a clearinghouse or payer.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A claim handling system for facilitating the real-time or near real time processing and payment of claims, said claim handling system comprising:
   a secure claim transmission application (SCTA) being configured for executing the following:
   receiving a plurality of claims from a practice management system, wherein each of said plurality of claims identifies a claim payer to which the claim is directed;
   encrypting each of said plurality of claims via a different encryption key to facilitate transmitting each of said plurality of claims to a claim server;
   directing each encrypted claim to said claim server in real time or near real time, wherein the claim server individually forwards each encrypted claim to a respective identified claim payer;
   receiving an encrypted claim response from said claim server for each of said plurality of claims, wherein said encrypted claim response corresponds to a response generated by said claim payer to a corresponding claim transmitted to said claim payer by said claim server;
   decrypting each one of said encrypted claim responses corresponding to each one of said plurality of claims; and
   making available each of said decrypted claim responses to said practice management system,
   wherein each decrypted claim response is received by said SCTA in real-time or near real-time in response to the transmission to said claim server of said claim corresponding to said decrypted claim response.

2. The claim handling system of claim 1, wherein said SCTA is further configured for configuring each one of said plurality of claims for transmission to a claim server.

3. The claim handling system of claim 2, wherein said SCTA is further configured for altering said format of each of one of said plurality of claims prior to their respective transmission to said claim server.

4. The claim handling system of claim 1, wherein said SCTA is further configured for setting up a secure session with said claim server through which at least one of said plurality of claims is transmitted to said claim server.

5. The claim handling system of claim 4, wherein said SCTA is further configured for exchanging secure tokens with said claim server to set up said secure connection with said claim server.

6. The claim handling system of claim 1, wherein said SCTA is further configured for identifying a header within at least one of said plurality of claims, wherein said header identifies said at least one of said plurality of claims as directed to said payer.

7. The claim handling system of claim 1, wherein encrypting each of said plurality of claims via a different encryption key to facilitate transmitting each of said plurality of claims to a claim server further comprises:
   requesting a secure connection with said claim server;
   receiving a secure connection response from said claim server; and
   examining said secure connection response to verify the authenticity of said claim server.

8. The claim handling system of claim 1, wherein making available each of said decrypted claim responses to said practice management system comprises allowing the practice management system to reach each of said claim responses from a serial interface controlled by said SCTA.

9. The claim handling system of claim 1, wherein making available each of said decrypted claim responses to said practice management system comprises allowing the practice management system to read each of said claim responses from a directory controlled by said SCTA.

10. A method for facilitating the real-time or near real time processing of claims, comprising:
    receiving a plurality of claims from a practice management system, wherein each one of said plurality of claims identifies a claim payer to which the claim is directed;
    encrypting each of said plurality of claims via a different encryption key to facilitate transmitting each of said plurality of claims to a claim server;
    directing each encrypted claim to said claim server in real time or near real time, wherein the claim server individually forwards each encrypted claim to a respective identified claim payer;
    receiving an encrypted claim response from said claim server for each of said plurality of claims, wherein said encrypted claim response corresponds to a response generated by said claim payer to a corresponding claim transmitted to said claim payer by said claim server;
    decrypting each one of said encrypted claim responses corresponding to each of said plurality of claims; and
    making available each of said decrypted claim responses to said practice management system,
    wherein each decrypted claim response is received by said practice management system in real-time or near real-time in response to the transmission to said claim server of said claim corresponding to said decrypted claim response.

11. The method of claim 10, further comprising configuring each of said plurality of claims for transmission to a claim server.

12. The method of claim 11, further comprising altering said format of each of said plurality of claims prior to their respective transmission to said claim server.

13. The method of claim 10, further comprising setting up a secure session with said claim server through which at last of said plurality of claims is transmitted to said claim server.

14. The method of claim 13, further comprising exchanging secure tokens with said claim server to set up said secure connection with said claim server.

15. The method of claim 10, further comprising identifying a header within at least one of said plurality of claims, wherein said header identifies said at least one of said plurality of claims as directed to said payer.

16. The method of claim 10, wherein encrypting each of said plurality of claims via a different encryption key to facilitate transmitting each of said plurality of claims to a claim server further comprises:
    requesting a secure connection with said claim server;
    receiving a secure connection response from said claim server; and
    examining said secure connection response to verify the authenticity of said claim server.

17. The method of claim 10, wherein making available each of said decrypted claim responses to said practice management system comprises allowing the practice management system to read each of said claim responses from a serial interface to which the claim responses were written.

18. The claim handling system of claim 10, wherein making available each of said decrypted claim responses to said practice management system comprises allowing the practice management system to read each of said claim responses from a directory to which the claim responses were written.

* * * * *

UNITED STATES PATENT AND TRADEMARK OFFICE
CERTIFICATE OF CORRECTION

| | | |
|---|---|---|
| PATENT NO. | : 7,370,018 B2 | Page 1 of 1 |
| APPLICATION NO. | : 10/133001 | |
| DATED | : May 6, 2008 | |
| INVENTOR(S) | : Oliver Ross Bryant, Jr., Scott N. Frazor and James Couser Rowe, III | |

It is certified that error appears in the above-identified patent and that said Letters Patent is hereby corrected as shown below:

At column 2, line 64, delete "patent" and insert --patient--.

At column 12, line 55, delete "outfox" and insert --outbox--.

At column 12, line 66, delete "outfox" and insert --outbox--.

At column 13, line 52, after "link" delete "28".

At column 16, line 50, after "at" delete "last" and insert --least one--.

At column 16, line 58, after "said" insert --claim--.

Signed and Sealed this

Sixteenth Day of September, 2008

JON W. DUDAS
*Director of the United States Patent and Trademark Office*